(12) United States Patent
Xu et al.

(10) Patent No.: US 10,583,074 B2
(45) Date of Patent: Mar. 10, 2020

(54) ORAL CARE COMPOSITIONS

(71) Applicant: Colgate-Palmolive Company, New York, NY (US)

(72) Inventors: Shao Peng Xu, Guangzhou (CN); Peng Yan, Guangzhou (CN); Ying Yang, Monmouth Junction, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/828,511

(22) Filed: Dec. 1, 2017

(65) Prior Publication Data
US 2019/0167555 A1    Jun. 6, 2019

(51) Int. Cl.
| *A61K 8/34* | (2006.01) |
| *A61K 8/36* | (2006.01) |
| *A61Q 11/00* | (2006.01) |
| *A61K 8/63* | (2006.01) |

(52) U.S. Cl.
CPC .............. *A61K 8/63* (2013.01); *A61K 8/347* (2013.01); *A61K 8/36* (2013.01); *A61Q 11/00* (2013.01)

(58) Field of Classification Search
CPC . A61K 8/63; A61K 8/347; A61K 8/36; A61Q 11/00
See application file for complete search history.

(56) References Cited

U.S. PATENT DOCUMENTS

| 8,263,048 B2 * | 9/2012 | Yang | A61K 8/24 424/401 |
| 2009/0087501 A1 | 4/2009 | Cummins | |
| 2012/0244085 A1 | 9/2012 | Trivedi et al. | |

FOREIGN PATENT DOCUMENTS

JP    H11-29468    2/1999

OTHER PUBLICATIONS

Kim et al. "Enhancement of Platelet Aggregation by Ursolic Acid and Oleanolic Acid", Biomolecules and Therapeutics, 22(3), pp. 254-259, 2014.*
Ajiboye et al., 2016, "Antibacterial activity of Syzygium aromaticum seed: Studies on oxidative stress biomarkers and membrane permeability," Microbial Pathogenesis 95:208-215.
Anandjiwala et al., 2006, "Quantification of eugenol, luteolin, ursolic acid, and oleanolic acid in black (Krishna tulasi) and green (Sri tulasi) varieties of *Ocimum sanctum* Linn. Using high-performance thin-layer chromatography," Journal of AOAC International 89(6):1467-1474.
Gupta et al., 2014, "A randomized controlled clinical trial of Ocimum sanctum and chlorhexidine mouthwash on dental plaque and gingival inflammation," Journal of Ayurveda and Integrative Medicine 5(2):109-116.
International Search Report and Written Opinion of the International Searching Authority in International Application No. PCT/US2017/064114, dated Feb. 9, 2018.
Meng, 2017, "Anti-bacterial toothpaste comprises anti-inflammatory hemostatic component anti-allergic and analgesic component and base component," Database WPI Thomson Scientific AN 2017-192907 & CN 106491379.
Shenqing, 2017, "Feminine health wine for relieving physical fatigue and preparation method thereof," Database CAS AN 166:372220 & CN 106520426A.

\* cited by examiner

*Primary Examiner* — Lezah Roberts

(57) ABSTRACT

Oral care compositions including a hemostatic agent, wherein the hemostatic agent includes a mixture of oleanic acid and eugenol. Methods of making and using these compositions are also described.

9 Claims, No Drawings

ORAL CARE COMPOSITIONS

BACKGROUND

Gum bleeding is associated with many common oral conditions, such as gingivitis. Gum bleeding may be caused by a buildup of plaque, a soft, sticky, colorless film of bacteria that forms on the teeth and gums, and produces toxins that may inflame or infect the gum tissue to cause gingivitis. Gingivitis is the initial stage of gum disease and, if left untreated, may cause periodontitis.

Antibacterial agents have been used in oral care products to reduce plaque and gingivitis, and hence reduce gum bleeding. Similarly, coagulant agents have also been used in oral care products to reduce gum bleeding. However, the antibacterial efficacy of compounds may be affected by other active ingredients in the oral care product, and some coagulant agents, such as tranexamic acid, carry increased thromboembolic and drug interaction risks.

Accordingly, it would be useful to develop oral care compositions, such as toothpastes and mouthwashes, configured to provide improved gum bleeding relief and antibacterial efficacy. Additionally, it would be useful to develop oral care composition with natural or botanically-based active ingredients.

BRIEF SUMMARY

This summary is intended merely to introduce a simplified summary of some aspects of one or more embodiments of the present disclosure. Further areas of applicability of the present invention will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing an oral care composition, including from 0.04 weight % to 2.80 weight % hemostatic agent, based on a total weight of the oral care composition, wherein the hemostatic agent comprises a mixture of oleanic acid and at least one of eugenol, methyl eugenol, or iso-eugenol.

In another embodiment, the oral care composition may include from 0.10 weight % to 1.0 weight % hemostatic agent.

In another embodiment, the hemostatic agent includes a mixture of oleanic acid and eugenol.

In another embodiment, the hemostatic agent includes from 0.02 weight % to 2.0 weight % oleanic acid, based on the total weight of the oral care composition; and from 0.01 weight % to 0.8 weight % eugenol, based on the total weight of the oral care composition.

In another embodiment, the hemostatic agent includes from 0.05 weight % to 0.50 weight % oleanic acid; and from 0.05 weight % to 0.25 weight % eugenol.

In another embodiment, the hemostatic agent includes 0.10 weight % oleanic acid; and 0.05 weight % eugenol.

In another embodiment, the hemostatic agent increases the platelet aggregation area by at least 10% over a control when tested according to example 1.

In another embodiment, the hemostatic agent increases the platelet aggregation area by at least 20% over a control when tested according to example 1.

In another embodiment, the hemostatic agent decreases the platelet rolling velocity by at least 10% over a control when tested according to example 1.

In another embodiment, the hemostatic agent decreases the platelet rolling velocity by at least 20% over a control when tested according to example 1.

In another embodiment, other than the hemostatic agent, the oral care composition does not include another antibacterial agent.

The foregoing and/or other aspects and utilities embodied in the present disclosure may be achieved by providing a method for increasing the hemostatic effect of an oral care composition, including adding a hemostatic agent to the oral care composition, wherein the hemostatic agent includes a mixture of oleanic acid and at least one of eugenol, methyl eugenol, or iso-eugenol.

The foregoing and/or other aspects and utilities embodied in the present disclosure may be achieved by providing a method of reducing gum bleeding in an oral cavity of a subject, including administering the oral care composition of any one of the claims 1-12 to the oral cavity of the subject in an amount sufficient to reduce gum bleeding.

The foregoing and/or other aspects and utilities embodied in the present disclosure may be achieved by using the oral care composition to reduce gum bleeding, wherein the oral care composition includes from 0.04 weight % to 2.80 weight % hemostatic agent, based on a total weight of the oral care composition, wherein the hemostatic agent comprises a mixture of oleanic acid and at least one of eugenol, methyl eugenol, or iso-eugenol.

DETAILED DESCRIPTION

Reference will now be made in detail to the various embodiments in the present disclosure. The embodiments are described below to provide a more complete understanding of the components, processes, compositions, and apparatuses disclosed herein. Any examples given are intended to be illustrative, and not restrictive. However, it will be apparent to one of ordinary skill in the art that the invention may be practiced without these specific details. In other instances, well-known methods, procedures, and components have not been described in detail so as not to unnecessarily obscure aspects of the embodiments.

Throughout the specification and claims, the following terms take the meanings explicitly associated herein, unless the context clearly dictates otherwise. Phrases such as "in an embodiment," "in certain embodiments," and "in some embodiments" as used herein do not necessarily refer to the same embodiment(s), though they may. Furthermore, the phrases "in another embodiment" and "in some other embodiments" as used herein do not necessarily refer to a different embodiment, although they may. As described below, various embodiments may be readily combined, without departing from the scope or spirit of the present disclosure.

As used herein, the term "or" is an inclusive operator, and is equivalent to the term "and/or," unless the context clearly dictates otherwise. The term "based on" is not exclusive and allows for being based on additional factors not described, unless the context clearly dictates otherwise. In the specification, the recitation of "at least one of A, B, and C," includes embodiments containing A, B, or C, multiple examples of A, B, or C, or combinations of A/B, A/C, B/C, A/B/B/B/B/C, A/B/C, etc. In addition, throughout the specification, the meaning of "a," "an," and "the" include plural references. The meaning of "in" includes "in" and "on."

It will also be understood that, although the terms first, second, etc. may be used herein to describe various elements, these elements should not be limited by these terms. These terms are only used to distinguish one element from another. For example, a first object, component, or step could be termed a second object, component, or step, and, similarly, a second object, component, or step could be termed a first object, component, or step, without departing from the scope of the invention. The first object, component, or step, and the second object, component, or step, are both, objects, components, or steps, respectively, but they are not to be considered the same object, component, or step. It will be further understood that the terms "includes," "including," "comprises" and/or "comprising," when used in this specification, specify the presence of stated features, steps, operations, elements, and/or components, but do not preclude the presence or addition of one or more other features, steps, operations, elements, components, and/or groups thereof. Further, as used herein, the term "if" may be construed to mean "when" or "upon" or "in response to determining" or "in response to detecting," depending on the context.

All physical properties that are defined hereinafter are measured at 20° to 25° Celsius unless otherwise specified.

When referring to any numerical range of values herein, such ranges are understood to include each and every number and/or fraction between the stated range minimum and maximum, as well as the endpoints. For example, a range of 0.5-6% would expressly include all intermediate values of, for example, 0.6%, 0.7%, and 0.9%, all the way up to and including 5.95%, 5.97%, and 5.99%, among many others. The same applies to each other numerical property and/or elemental range set forth herein, unless the context clearly dictates otherwise.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith.

Unless otherwise specified, all percentages and amounts expressed herein and elsewhere in the specification should be understood to refer to percentages by weight. The amounts given are based on the active weight of the material.

With regard to procedures, methods, techniques, and workflows that are in accordance with some embodiments, some operations in the procedures, methods, techniques, and workflows disclosed herein may be combined and/or the order of some operations may be changed.

An oral care composition as disclosed herein includes a hemostatic agent. In certain embodiments, the hemostatic agent reduces the amount of gum bleeding by increasing the platelet aggregation in blood leading to hemostasis. An increase in hemostasis may be evidenced by a higher platelet aggregation area and/or a lower platelet rolling velocity. In certain embodiments, the hemostatic agent simultaneously provides an antibacterial effect. In certain embodiments, the hemostatic agent includes oleanic acid, eugenol, and/or a mixture thereof. For example, the hemostatic agent may be a synergistic combination of oleanic acid and eugenol. In some embodiments, the hemostatic agent is derived from or based upon compounds or extracts isolated from plants.

Formula 1 illustrates a chemical structure of oleanic acid. Oleanic or oleanolic acid (3β-hydroxy-olea-12-en-28-oic) is a pentacyclic triterpenoid that is widely distributed in plants.

For example, oleanic acid may be extracted from a number of medicinal plants, such as *Calendula officinalis* L. (marigold), *Ligustrum lucidum* Ait (oleaceae), and *Hemsleyva Chinensis* Cogn.

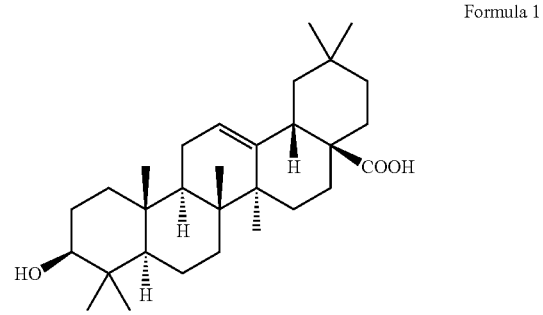

Formula 1

Oleanic acid is believed to have a variety of pharmacological effects, including anti-inflammatory, antioxidant, antimicrobial, and anticancer activities. In addition, in certain embodiments, oleanic acid is able to enhance platelet aggregation.

While not intending to be limited to any particular theory, it is believed that oleanic acid enhances platelet aggregation through the mediation of the phospholipase C-Calcium dependent signaling pathway. Platelet aggregation is the first step of hemostasis and has been recognized as an important step for hemostatic plug formation. Accordingly, the enhancement of platelet aggregation may accelerate blood coagulation and help stop or reduce gum bleeding.

Formula 2 illustrates a chemical structure of eugenol. Eugenol (4-allyl-2-methoxyphenol), is a naturally occurring phenol essential oil extracted from, for example, cloves, nutmeg, cinnamon, basil, and bay leaf. Eugenol is believed to have both antioxidant and antimicrobial effects. In addition, in certain embodiments, eugenol is also able to enhance platelet aggregation. Eugenol may also be provided as methyl eugenol or iso-eugenol.

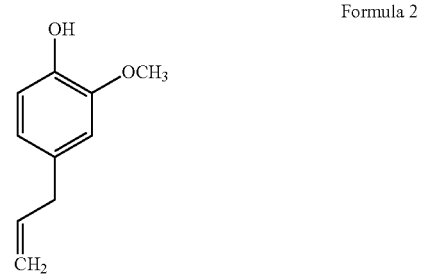

Formula 2

The inventors have surprisingly discovered that the combination of oleanic acid and eugenol have increased platelet aggregation effects. In some embodiments, the platelet aggregation effects of oleanic acid combined with eugenol are greater than those of oleanic acid or eugenol separately. In addition, oral care compositions including oleanic acid and eugenol also provide antibacterial and/or antimicrobial effect.

Accordingly, as described in the present disclosure, the oral care composition includes a hemostatic agent including oleanic acid, eugenol, and/or a mixture thereof. For example, the hemostatic agent is a synergistic combination of an effective amount of oleanic acid and eugenol, methyl eugenol, and/or iso eugenol.

In some embodiments, the hemostatic agent includes only oleanic acid or eugenol. In other embodiments, the hemostatic agent includes a combination of oleanic acid and eugenol.

In certain embodiments, a hemostatic agent including the oleanic acid and eugenol combination is the only hemostatic agent present in the oral care composition. In other embodiments, the oral care composition includes no other agents to reduce gum bleeding apart from the hemostatic agent. In some embodiments, the oral care composition includes no other antibacterial agents apart from the hemostatic agent.

In certain embodiments, the oral care composition includes from about 0.04 weight % to about 2.8 weight % hemostatic agent, based on the total weight of the oral care composition. For example, the oral care composition includes from about 0.05 weight % to about 2.0 weight % hemostatic agent, from about 0.1 weight % to about 1 weight % hemostatic agent, or from about 0.1 weight % to about 0.5 weight % hemostatic agent, based on the total weight of the oral care composition.

In other embodiments, the oral care composition includes 3 weight % or less, 2 weight % or less, 1 weight ° % or less, 0.5 weight %, or 0.25 weight % or less hemostatic agent, based on the total weight of the oral care composition.

In certain embodiments, the oral care composition includes from 0.01 weight % to 0.30 weight % hemostatic agent, based on the total weight of the oral care composition. For example, the oral care composition includes from 0.05 weight % to 0.25 weight % or from 0.10 weight % to 0.20 weight % hemostatic agent. In one preferred embodiment, the oral care composition may include 0.15 weight % hemostatic agent.

In certain embodiments, the oral care composition includes from about 0.02 weight % to about 2.0 weight % oleanic acid, based on the total weight of the oral care composition. For example, the oral care composition includes from about 0.05 weight % to about 1.0 weight %, from about 0.05 weight % to about 0.5 weight %, from about 0.1 weight % to about 0.25 weight %, or from about 0.1 weight % to about 0.2 weight % oleanic acid, based on the total weight of the oral care composition. In one preferred embodiment, the oral care composition may include 0.10 weight % oleanic acid.

In certain embodiments, the oral care composition includes from 0.01 weight % to 0.8 weight % eugenol, based on the total weight of the oral care composition. For example, the oral care composition includes from about 0.02 weight % to about 0.6 weight %, from about 0.04 weight % to about 0.2 weight %, or from about 0.05 weight % to about 0.10 weight % eugenol, based on the total weight of the oral care composition. In a preferred embodiment, the oral care composition may include 0.05 weight % eugenol. In some embodiments, the oral care composition may include methyl eugenol and/or iso eugenol instead of or in addition to eugenol.

Generally, viscosity is an important parameter for oral care compositions, such as toothpastes or whitening gels. For example, when the viscosity of an oral care composition is too low, it may become too runny and physical phase separation may take place. In some cases, this will not only affect the aesthetics of the oral care composition but also the homogeneity of the ingredients in the oral care composition.

On the other hand, if the viscosity of the oral care compositions is too high, the oral care composition will be difficult to manufacture and package.

In addition, oral care compositions with high viscosity are very difficult for users to evacuate from commonly used packages, such as tubes or syringes. Accordingly, it's important to select ingredients for oral care compositions that achieve a desirable range of viscosity to ensure product manufacturability, stability, and quality, as well as consumer acceptance.

In some embodiments, the viscosity of the oral care composition is from about 10,000 centipoise (cPs) to about 500,000 cPs at 25° C. For example, the viscosity of the oral care composition is from about 50,000 cPs to about 400,000 cPs at 25° C. In one embodiment, the viscosity of the oral care composition is from about 125,000 cPs to about 300,000 cPs at 25° C.

In some embodiments, the oral care composition may include additional ingredients common to oral care compositions, such as carriers, dispersants, whitening agents, flavoring agents, tartar control agents, surfactants, sweeteners, humectants, colorants, antibacterial agents, preservatives, dyes, and pigments.

All ingredients used in the compositions described herein should be orally acceptable. "Orally acceptable" means an ingredient which is present in the composition as described in an amount and form which does not render the composition unsafe, unpalatable, or otherwise unsuitable for use in the oral cavity. In addition, the additional ingredients should not substantially inhibit the efficacy of the hemostatic agent described above.

In various embodiments of the present disclosure, the oral care composition includes an orally acceptable carrier. As used herein, an "orally acceptable carrier" refers to a material or combination of materials that are safe for use in the oral care compositions of the present disclosure while retaining significant efficacy for the hemostatic agent. In certain embodiments, the carrier is specifically selected to ensure that there is no substantially reduction in efficacy for the hemostatic agent. For example, the oral care composition may use water as the carrier. In certain embodiments, the oral care composition includes 90 weight % or less, 70 weight % or less, or 50 weight % or less carrier, based on the total weight of the oral care composition.

In certain embodiments, the oral care composition may include one or more humectants. In some embodiments, the humectant is a mixture of humectants, such as glycerin and sorbitol, and a polyhydric alcohol, such as propylene glycol, butylene glycol, hexylene glycol, polyethylene glycol. In certain embodiments, the oral care composition includes from 5 weight % to 40 weight % or from 10 weight % to 30 weight % humectant, based on a total weight of the oral care composition.

The oral care composition may include one or more whitening agent. As used herein, a "whitening agent" is a material that affects whitening of a tooth surface to which it is applied. For example, in some embodiments, the whitening agent is an oxidizing agent. In its broadest sense, "oxidizing agent" is intended to include those compounds which can accept an electron from another molecule in the environment of the oral cavity without having a deleterious or unacceptably harmful effect on the oral cavity in normal and accepted use.

In some embodiments, the whitening agent may include peroxides and hydroperoxides, such as hydrogen peroxide, peroxides of alkali and alkaline earth metals, organic peroxy compounds, peroxy acids, salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include urea peroxide, carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. Peroxy acids and their salts include organic peroxy acids such as alkyl peroxy acids, and monoperoxyphthalate and mixtures thereof, as well as inorganic peroxy acid salts such as percarbonate, perphosphate, perborate and persilicate salts of alkali and alkaline earth metals such as lithium, potassium, sodium, magnesium, calcium and barium, and mixtures thereof. In some embodiments a non-peroxide whitening agent may be provided. Whitening agents among those useful herein include non-peroxy compounds, such as chlorine dioxide, chlorites and hypochlorites. Chlorites and hypochlorites include those of alkali and alkaline earth metals such as lithium, potassium, sodium, magnesium, calcium and barium. Non-peroxide whitening agents also include colorants, such as titanium dioxide and hydroxyapatite.

In some embodiments, the oral care composition includes from about 0.01% to about 50% whitening agent based on a total weight of the oral care composition. For example, the oral care composition includes from about 0.05 weight % to about 40 weight % whitening agent. In one embodiment, the oral care composition includes about 0.1 weight % whitening agent based on a total weight of the oral care composition.

In one embodiment, the oral care composition includes one or more surfactants. In some embodiments, the surfactants enhance stability of the composition, help clean the oral cavity surfaces through detergency, and provide foam upon agitation, e.g., during brushing with an oral care composition of the disclosure. Surfactants or surface active agents generally achieve increased whitening action by thoroughly dispersing the whitening agent throughout the oral cavity. In various embodiments, suitable surface active agents may function as a surface active agent, emulsifier, and/or foam modulator.

Any orally acceptable surfactant, most of which are anionic, nonionic, cationic, or amphoteric, may be used. A combination of surfactants may also be used. Suitable anionic surfactants include without limitation water-soluble salts of $C_{8-20}$ alkyl sulfates, sulfonated monoglycerides of $C_{8-20}$ fatty acids, sarcosinates, taurates and the like. Illustrative examples of these and other classes include sodium lauryl sulfate, sodium cocoyl monoglyceride sulfonate, sodium lauryl sarcosinate, sodium lauryl isoethionate, sodium laureth carboxylate, and sodium dodecyl benzenesulfonate. Suitable nonionic surfactants include without limitation poloxamers, polyoxyethylene sorbitan esters, fatty alcohol ethoxylates, alkylphenol ethoxylates, tertiary amine oxides, tertiary phosphine oxides, dialkyl sulfoxides and the like. Suitable amphoteric surfactants include, without limitation, derivatives of $C_{8-20}$ aliphatic secondary and tertiary amines having an anionic group such as carboxylate, sulfate, sulfonate, phosphate or phosphonate. A suitable example is cocoamidopropyl betaine.

In some embodiments, the oral care composition includes from about 0.01% to about 20.0% surfactant based on a total weight of the oral care composition. For example, the oral care composition includes from about 1.0 weight % to about 10.0 weight % surfactant. In one embodiment, the oral care composition includes about 2 weight % surfactant based on a total weight of the oral care composition. For example, the oral care composition may include about 2 weight % sodium lauryl sulfate.

In certain embodiments, the oral care composition may include thickening agents or thickeners. Any orally acceptable thickening agent may be used, including without limitation carbomers, also known as carboxyvinyl polymers, carrageenans, also known as Irish moss and more particularly carrageenan (iota-carrageenan), high molecular weight polyethylene glycols (such as CARBOWAX™, available from The Dow Chemical Company), cellulosic polymers such as hydroxyethylcellulose, carboxymethylcellulose ("CMC") and salts thereof, e.g., CMC sodium, natural gums such as karaya, xanthan, gum arabic and tragacanth, colloidal magnesium aluminum silicate, and colloidal or fumed silica and mixtures of the same. The thickening agent may be a combination of one or more orally acceptable thickening agents.

In some embodiments, the oral care composition includes from about 0.01% to about 30% thickening agent based on a total weight of the oral care composition. For example, the oral care composition includes from about 0.1 weight % to about 20 weight % thickening agent. In yet another example, the oral care composition includes from about 0.5 weight % to about 10 weight % thickening agent based on a total weight of the oral care composition. For example, the oral care composition may include about 3 weight % fumed silica.

In some embodiments, the oral care composition includes an antioxidant. Acceptable antioxidants include BHA, BHT, vitamin A, carotenoids, vitamin E, flavonoids, polyphenols, ascorbic acid, herbal antioxidants, chlorophyll, melatonin and mixtures thereof. In some embodiments, the oral care composition includes from about 0.001% to about 1% antioxidants based on a total weight of the oral care composition. In one embodiment, the oral care composition includes about 0.03 weight % antioxidant by weight.

In certain embodiments, the oral care composition includes one or more flavoring agents. Useful flavoring agents include any material or mixture of materials operable to enhance the taste of the oral care composition. Any orally acceptable natural or synthetic flavoring agent may be used, such as flavoring oils, flavoring aldehydes, esters, alcohols, similar materials, and combinations thereof. Flavoring agents include vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants, and mixtures thereof. Also encompassed within flavoring agents herein are ingredients that provide fragrance and/or other sensory effect in the mouth, including cooling or warming effects. Such ingredients include menthol, menthyl acetate, menthyl lactate, camphor, eucalyptus oil, eucalyptol, anethole, eugenol, cassia, oxanone, x-irisone, propenyl guaiethol, thymol, linalool, benzaldehyde, cinnamaldehyde, N-ethyl-p-menthan-3-carboxamine, N,2,3-trimethyl-2-isopropylbutanamide, 3-1-menthoxypropane-1,2-diol, cinnamaldehyde glycerol acetal (CGA), methone glycerol acetal (MGA) and mixtures thereof.

In some embodiments, the oral care composition includes from about 0.01% to about 5% flavoring agents based on a total weight of the oral care composition. For example, the oral care composition includes from about 0.05 weight % to about 3 weight % flavoring agents. In yet another embodiment, the oral care composition includes from about 0.1 weight % to about 3 weight %, from about 0.2 weight % to about 2.5 weight %, or about 1.5 weight % flavoring agents based on a total weight of the oral care composition. For example, the oral care composition may include about 1.5 weight % of dental cream flavor.

In some embodiments, the oral care composition may also include one or more sweeteners. Sweeteners among those useful herein include orally acceptable natural or artificial, nutritive or non-nutritive sweeteners. Such sweeteners include dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof, sucralose, dipeptide-based intense sweeteners, cyclamates, dihydrochalcones and mixtures thereof. Some embodiments may include one or more sweeteners. In some embodiments, the oral care composition includes from about 0.005% to about 5% sweeteners based on a total weight of the oral care composition. In other embodiments, the oral care composition includes from about 0.01% to about 1% sweeteners based on a total weight of the oral care composition. For example, the oral care composition may include about 0.5 weight % sodium saccharin and about 0.04 weight % sucralose.

In some embodiments, the oral care composition may include colorants. Colorants, such as dyes or pigments, may be food color additives presently certified under the Food Drug & Cosmetic Act for use in food and ingested drugs, including dyes such as FD&C Red No. 3 (sodium salt of tetraiodofluorescein), Food Red 17, disodium salt of 6-hydroxy-5-((2-methoxy-5-methyl-4-sulphophenyl)azo)-2-naphthalenesulfonic acid, Food Yellow 13, sodium salt of a mixture of the mono and disulphonic acids of quinophtalone or 2-(2-quinolyl) indanedione, FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylamino)-phenyl]-(4-hydroxy-2-sulfoniumphenyl)-methylene}-[1-(N-ethyl-N-p-sulfobenzyl)-DELTA-3,5-cyclohexadienimine], FD&C Blue No. 1 (disodium salt of dibenzyldiethyl-diamino-triphenylcarbinol trisulfonic acid anhydrite), FD&C Blue No. 2 (sodium salt of disulfonic acid of indigotin) and mixtures thereof in various proportions. Typically, colorants, if included, are present in very small quantities.

In some embodiments, the oral care composition may also include one or more pH modifying agents. The pH modifying agents among those useful herein include acidifying agents to lower pH, basifying agents to raise pH and buffering agents to control pH within a desired range. For example, one or more compounds selected from acidifying, basifying and buffering agents can be included to provide a pH of 2 to 10, or in various embodiments from about 2 to about 8, from about 3 to about 9, from about 4 to about 8, from about 5 to about 7, from about 6 to about 10, and from about 7 to about 9. Any orally acceptable pH modifying agent may be used, including without limitation carboxylic, phosphoric and sulfonic acids, acid salts (e.g., monosodium citrate, disodium citrate, monosodium malate, etc.), alkali metal hydroxides such as sodium hydroxide, carbonates such as sodium carbonate, bicarbonates, sesquicarbonates, borates, silicates, phosphates (e.g., monosodium phosphate, trisodium phosphate, pyrophosphate salts, etc.), imidazole and mixtures thereof. One or more pH modifying agents are optionally present in a total amount effective to maintain the composition in an orally acceptable pH range. In some embodiments, the oral care composition includes from about 0.01% to about 10% pH modifier agents based on a total weight of the oral care composition. For example, the oral care composition may include about 0.9 weight % sodium acid pyrophosphate (SAPP) and about 2 weight % tetrasodium pyrophosphate (TSPP) as a pH modifier.

The oral care composition may include one or more antibacterial agents or preservatives. In some embodiments, the preservatives improve an antimicrobial characteristic of the oral care composition to improve storage life or prevent decay.

In certain embodiments, the one or more antibacterial agents or preservatives include at least one of sodium benzoate, methyl paraben, ethyl paraben, zinc citrate, zinc oxide, triclosan, stannum salts, and combinations thereof.

The oral care composition may include an effective amount of antibacterial agents or preservatives. For example, the oral care composition may include an amount of antibacterial agents or preservatives effective to reduce a spoilage of the oral care composition during storage or use.

The oral care composition of the present disclosure may also include one or more additional active ingredients, which are operable for the prevention or treatment of a condition or disorder of hard or soft tissue of the oral cavity, the prevention or treatment of a physiological disorder or condition, or to provide a cosmetic benefit.

Some embodiments of the present disclosure include a dental abrasive or combination of dental abrasive agents. As used herein, the term "abrasive" or "abrasive agent" also includes materials commonly referred to as "polishing agents." Any orally acceptable abrasive may be used, but typically, type, fineness (particle size) and amount of abrasive should be selected so that tooth enamel is not excessively abraded in normal use of the composition. Suitable abrasives include without limitation silica (in the form of silica gel, hydrated silica or precipitated silica), alumina, insoluble phosphates, calcium carbonate, resinous abrasives such as urea-formaldehyde condensation products and the like.

Among insoluble phosphates useful as abrasives are orthophosphates, polymetaphosphates and pyrophosphates. Illustrative examples are dicalcium orthophosphate dihydrate, calcium pyrophosphate, n-calcium pyrophosphate, tricalcium phosphate, calcium polymetaphosphate and insoluble sodium polymetaphosphate.

Average particle size of an abrasive, if present, is generally from about 0.1 to 100 about µm. For example, the particle size may be from about 1 to about 80 µm or from about 5 to about 60 µm. In some embodiments, one or more abrasives are present in an amount of from about 0.01% to about 70% by weight, based on the total weight of the oral care composition. In other embodiments, the oral care composition includes from about 0.1 weight % to about 60 weight % abrasives. In some embodiments, the abrasive is calcium pyrophosphate. In some embodiments, the oral care composition includes from 0.01 weight % to about 70 weight % calcium pyrophosphate based on a total weight of the oral care composition. In another embodiment, the oral care composition includes about 20 weight % calcium pyrophosphate.

In various embodiments of the present disclosure, the oral care composition includes an anticalculus agent. Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. In some embodiments, the anticalculus agent is present in an amount of from about 0.01% to about 30% weight based on the total weight of the oral care composition. In some embodiments, the oral care composition includes a mixture of anticalculus agents. In some embodiments, tetrasodium pyrophosphate (TSPP) and sodium tripolyphosphate (STPP) are used as the anticalculus agents. In some embodiments, the anticalculus agent includes from 0.1% to 10 weight % TSPP, or about 2 weight % TSPP.

The oral care compositions of the present disclosure may also include a synthetic anionic polymeric polycarboxylate. The synthetic anionic polymeric polycarboxylate may act as a stabilizer for the polyphosphate anti-tartar agent and may help to block access of painful or pain-causing materials, such as sugars, to the tooth nerves.

In some embodiments, the oral care composition optionally includes a source of fluoride ions. In some embodiments, the source of fluoride ions is selected from: fluoride, monofluorophosphate (MFP), and fluorosilicate salts. In some embodiments, one or more fluoride ion-releasing compounds are optionally present in an amount providing a total of 100 to 20,000 ppm, 200 to 5,000 ppm, or 500 to 2,500 ppm, fluoride ions. If present, in some embodiments, the amount of fluoride source in the oral care composition ranges from about 0.01% to about 10% by weight, based on the total weight of the oral care composition, typically about 0.5% to about 1.5 weight %. For example, the oral care composition may include about 0.76 weight % MFP.

The compositions also may include a stannous ion or a stannous ion source to mitigate calcium loss. Suitable stannous ion sources include without limitation stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide and the like. In some embodiments, one or more stannous ion sources are included in the oral care composition. For example, the oral care composition may include from about 0.01% to about 10% stannous ion source by weight, based on the total weight of the oral care composition. In one embodiment, the oral care composition includes from about 0.1 weight % to about 7 weight % stannous ion source or from about 0.2 weight % to about 5 weight % stannous ion source.

EXAMPLES

Aspects of the present disclosure may be further understood by referring to the following examples. The examples are illustrative, and are not intended to be limiting embodiments thereof. Table 1 illustrates an oral care composition according to embodiments of the present disclosure and two comparative examples. The compositions of Table 1 had the same amount for all ingredients except that Oral Care Composition Example 1 included both oleanic acid and eugenol, while Comparative Example A and Comparative Example B included only oleanic acid or eugenol, respectively.

TABLE 1

| Ingredient | Example 1 | Comparative Example A | Comparative Example B |
|---|---|---|---|
| Oleanolic Acid | 0.1% | 0.1% | — |
| Eugenol | 0.05% | — | 0.05% |
| Sorbitol | | 31% | |
| Carrageenan | | 1.0% | |
| Dicalcium Phosphate Dihydrate | | 45% | |
| Betaine | | 0.22% | |
| Flavor | | 1.3% | |
| Sodium lauryl sulfate (SLS) | | 2.33% | |
| Sodium monofluorophosphate | | 1.1% | |
| Tetra sodium pyrophosphate | | 0.5% | |
| Sodium Saccharin | | 0.25% | |
| Water and minors | q.s | q.s | q.s |

Table 2 describes platelet aggregation area data for Example 1 and Comparative Examples A and B. Table 3 describes platelet rolling velocity data for Example 1 and Comparative Examples A and B. As described above, platelet aggregation area and platelet rolling velocity may be used to determine a hemostatic effect of oral care compositions.

Example 1

Blood platelets were obtained and purified from healthy human donors as follows: 10 mL of Human blood was collected in an anticoagulation tube and centrifuged at 150 g for 15 minutes at room temperature. After that, the upper platelet rich plasma (PRP) layer was aspirated into another centrifuge tube and centrifuged at 900 g for 15 minutes at room temperature. The upper platelet poor plasma (PPP) layer was aspirated, and 1 mL of PBS buffer was added to re-suspend the deposited platelets in the 15 ml centrifuge tube to create a suspended platelet solution. The suspended platelet solution was placed under a microscope (AXIO OBSERVER A1, Zeiss AG, Jena, Germany) and the number of platelets was counted with a haemocytometer. Sample platelet suspension tubes containing $3$-$6 \times 10^5$ platelets/mL were then prepared, each with 5 mL of PBS volume.

A flow chamber assay was then performed to measure platelet aggregation area and platelet rolling velocity as follows: 20 μL of 200 μg/mL collagen was incubated on a 35 mm petri dish (in central 5 mm×2.5 mm region) overnight (15-18 hours) at 4° C. The petri dishes were then washed with 1% BSA PBS buffer 3 times and incubated with 1% BSA PBS solution for 0.5 hours at room temperature. A flow chamber system (GLYCOTECH parallel-plate flow chamber, GlycoTech Corp., Gaithersburg, Md.) was set up and the platelet suspension was infused with a 0.04 mL/min (1 dyn/cm$^2$) flow for 3 minutes. The flow rate was then changed to 0.004 mL/min (0.1 dyn/cm$^2$) to reference blood shear stress in oral capillary vessels for 3 minutes, and a high speed camera (50 fps—MIKROTRON MC1310, Mikrotron GmbH Unterschleissheim, Germany) was used to record 2 minutes of the base platelet rolling behavior (control sample). The flow was then stopped and the rest volume of the platelet suspension was observed. 10 μL of the Example 1, Comparative Examples A, or Comparative Example B composition was then added to the platelet suspension. The platelet suspension was then infused with a 0.32 mL/min (8 dyn/cm$^2$) flow for 4 minutes (total 1.2 mL suspension). The flow rate was then changed to 0.004 mL/min (0.1 dyn/cm$^2$) for 3 minutes, and a high speed camera (50 fps) was used to record 2 minutes of the platelet rolling behavior after addition of the Example 1 and Comparative Examples A and B compositions (active samples).

The platelet aggregation area and platelet rolling velocity data was analyzed and tracked with image analysis software (IMAGE PRO PLUS available from Media Cybernetics, Silver Spring, Md.) and calculated as follows:

Platelet Aggregation Area

The sum area of adhered platelets at different times (30 sec, 60 sec, 120 sec) was measured from the 2 minute high speed recording for each platelet solution sample. The increase in platelet aggregation area for each sample at 120 seconds over the control sample was then calculated using the following formula and averaged over three measurements for each sample:

$$\text{Platelet Aggregation Area(120 seconds)} = 100 \times \frac{(\text{sum area of platelets} - \text{active sample}) - (\text{sum area of platelets} - \text{control sample})}{(\text{sum area of platelets} - \text{control sample})}$$

Platelet Rolling Velocity

Platelets having a mean diameter of 2.557+/−0.929 μm were selected to measure the average platelet rolling velocity. The rolling velocity for 50 platelets was captured and calculated from the 2 minute high speed recording for each platelet solution sample from the 90 second to the 120 second mark. The reduction in average platelet rolling velocity for each platelet solution over the control sample was then calculated using the following formula and averaged over three measurements for each sample:

$$\text{Platelet Rolling Velocity(90-120 seconds)} = 100 \times \frac{(\text{rolling velocity} - \text{control sample}) - (\text{rolling velocity} - \text{active sample})}{(\text{rolling velocity} - \text{control sample})}$$

TABLE 2

|  | Example 1 | Comparative Example A | Comparative Example B |
|---|---|---|---|
| Average Platelet Aggregation Area Increase over Control | 33.72% | 22.98% | 26.94% |

TABLE 3

|  | Example 1 | Comparative Example A | Comparative Example B |
|---|---|---|---|
| Average Platelet Rolling Velocity Decrease over Control | 26.76% | 15.21% | 22.23% |

As illustrated in Tables 2-3, compositions including oleanic acid or eugenol increase the average platelet aggregation area in platelet solutions and decrease the average platelet rolling velocity. However, as illustrated in Tables 2-3, the inventors have surprisingly discovered that the combination of oleanic acid and eugenol have synergistic effects resulting in an improved increase in average platelet aggregation area and improved decrease in average platelet rolling velocity and indicating improved hemostatic effects.

Table 4 illustrates the minimum inhibitory concentrations of antibacterial substances. That is, the amount in parts-per-million (ppm) required to inhibit the growth of common bacterial pathogens.

TABLE 4

| Sample | Solvent | Actinomyces viscosus ATCC 43137 | Lactobacillus casei ATCC 334 | Streptococcus oralis ATCC 35037 |
|---|---|---|---|---|
| Clove Oil | Ethanol | 250 ppm | 250 ppm | 125 ppm |
| Oleanic Acid | DMSO | 15.6 ppm | 7.8 ppm | 7.8 ppm |
| Eugenol | Ethanol | 250 ppm | 250 ppm | 250 ppm |
| Symrelief 100 | Ethanol | 125 ppm | 250 ppm | 62.5 ppm |
| Triclosan | Ethanol | 3.9 ppm | 7.8 ppm | 7.8 ppm |

Accordingly, in addition to having improved hemostatic effects, oral care compositions according to embodiment of the present disclosure are also able to provide simultaneous antibacterial effects.

The present disclosure has been described with reference to exemplary embodiments. Although a few embodiments have been shown and described, it will be appreciated by those skilled in the art that changes may be made in these embodiments without departing from the principles and spirit of preceding detailed description. It is intended that the present disclosure be construed as including all such modifications and alterations insofar as they come within the scope of the appended claims or the equivalents thereof.

What is claimed is:

1. An oral care composition, comprising:
   from 0.04 weight % to 2.80 weight % hemostatic agent, based on a total weight of the oral care composition,
   wherein the hemostatic agent comprises oleanic acid and eugenol,
   wherein the oleanic acid is from 0.05 weight % to 0.50 weight % based on the total weight of the oral care composition; and
   wherein the eugenol is from 0.05 weight % to 0.25 weight % based on the total weight of the oral care composition.

2. The oral care composition according to claim 1, comprising from 0.10 weight % to 1.0 weight % hemostatic agent.

3. The oral care composition according to claim 1, wherein the hemostatic agent comprises:
   0.10 weight % oleanic acid; and 0.05 weight % eugenol.

4. The oral care composition according to claim 1, wherein the hemostatic agent increases the platelet aggregation area by at least 10%.

5. The oral care composition according to claim 1, wherein the hemostatic agent increases the platelet aggregation area by at least 20%.

6. The oral care composition according to claim 1, wherein the hemostatic agent decreases the platelet rolling velocity by at least 10%.

7. The oral care composition according to claim 1, wherein the hemostatic agent decreases the platelet rolling velocity by at least 20%.

8. The oral care composition according to claim 1 wherein, other than the hemostatic agent, the oral care composition does not include another antibacterial agent.

9. A method of reducing gum bleeding in an oral cavity of a subject, comprising:
   administering the oral care composition according to claim 1 to the oral cavity of a subject in need thereof.

* * * * *